United States Patent [19]
Zalipsky et al.

[11] Patent Number: 5,534,259
[45] Date of Patent: Jul. 9, 1996

[54] POLYMER COMPOUND AND COATED PARTICLE COMPOSITION

[75] Inventors: Samuel Zalipsky, Fremont; Francis J. Martin, San Francisco, both of Calif.

[73] Assignee: Liposome Technology, Inc., Menlo Park, Calif.

[21] Appl. No.: 89,086

[22] Filed: Jul. 8, 1993

[51] Int. Cl.$^6$ .......................... A61K 9/127; A01N 25/26; A01N 25/28
[52] U.S. Cl. .......................... 424/450; 424/417; 424/489; 424/490; 424/491; 424/497; 264/4.1
[58] Field of Search .............................. 264/4.1; 424/489, 424/490, 491, 497, 450, 417

[56] References Cited

U.S. PATENT DOCUMENTS

| | | | |
|---|---|---|---|
| 4,830,857 | 5/1989 | Handjani et al. | 424/450 |
| 5,122,614 | 6/1992 | Zalipsky | 548/520 |
| 5,151,264 | 9/1992 | Samain et al. | 424/4.1 |

FOREIGN PATENT DOCUMENTS 88-76862  3/1988  Japan.

OTHER PUBLICATIONS

Domb, A. J., "Biodegradable Polymers Derived from Amino Acids," *Biomaterials* 11:686–689 (1990).
Ito, Y., et al., "Lipase Modification by Various Synthetic Polymers for Use in Chloroform," *Biotechnology Lett.* 14(12):1149–1152 (1992).
Szoka, F., and Papahadjopoulos, D., "Comparitive Properties and Methods of Preparation of Lipid Vesicles (Liposomes)," *Ann. Rev. Biophys. Bioeng.* 9:467–508 (1980).

Zalipsky, S., et al., "Attachment of Drugs to Polyethylene Glycols," *Eur. Polm. J.* 119(12):1177–1183 (1983).

*Primary Examiner*—Nathan M. Nutter
*Attorney, Agent, or Firm*—Peter J. Dehlinger; Judy M. Mohr

[57] ABSTRACT

A composition of polymer-coated particles, and a polymer compound used in forming the particles are disclosed. The polymer compound is composed of a hydrophilic polymer attached to a lipophilic moiety through a linking segment which contains chemical groups through which the compound can be crosslinked to other such compounds. The particles in the composition are prepared by forming lipid structures containing ordered arrays of the polymer compounds, and crosslinking the compounds through their chemical groups. The particles are used for parenteral administration of a pharmaceutical compound which is entrapped in the particles.

21 Claims, 14 Drawing Sheets

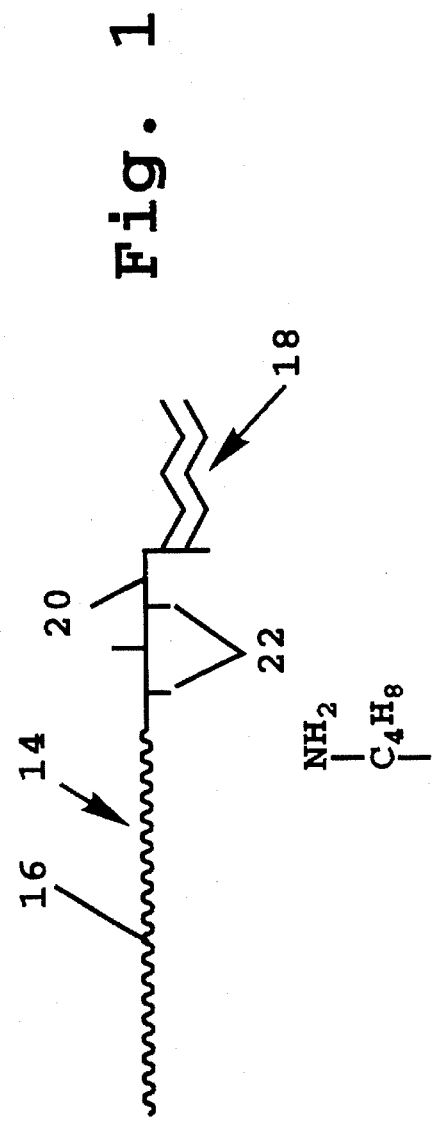
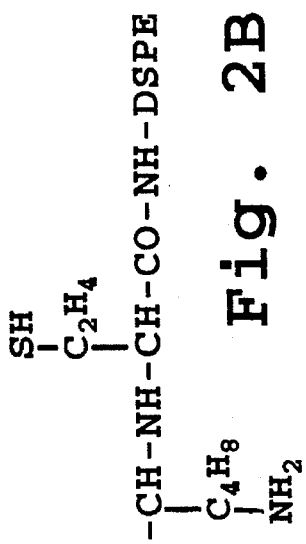
Fig. 1
Fig. 2A  CH₃(O-CH₂CH₂)ₙ-NH-(CO-CH-N)₃-CO-(CH₂)₆-CO-NH-DSPE with NH₂-C₄H₈ substituent
Fig. 2B  CH₃(OCH₂CH₂)ₙNHCO-CH-NH-CH-CH-CO-NH-DSPE with SH-C₂H₄ and C₄H₈-NH₂ substituents
Fig. 2C  CH₃(OCH₂CH₂)ₙNH-CO—CH₂-CH₂-CO-O-[inositol with OH groups and O-DSP]
Fig. 2D  CH₃(OCH₂CH₂)ₙ—N-DSPE with acryloyl group

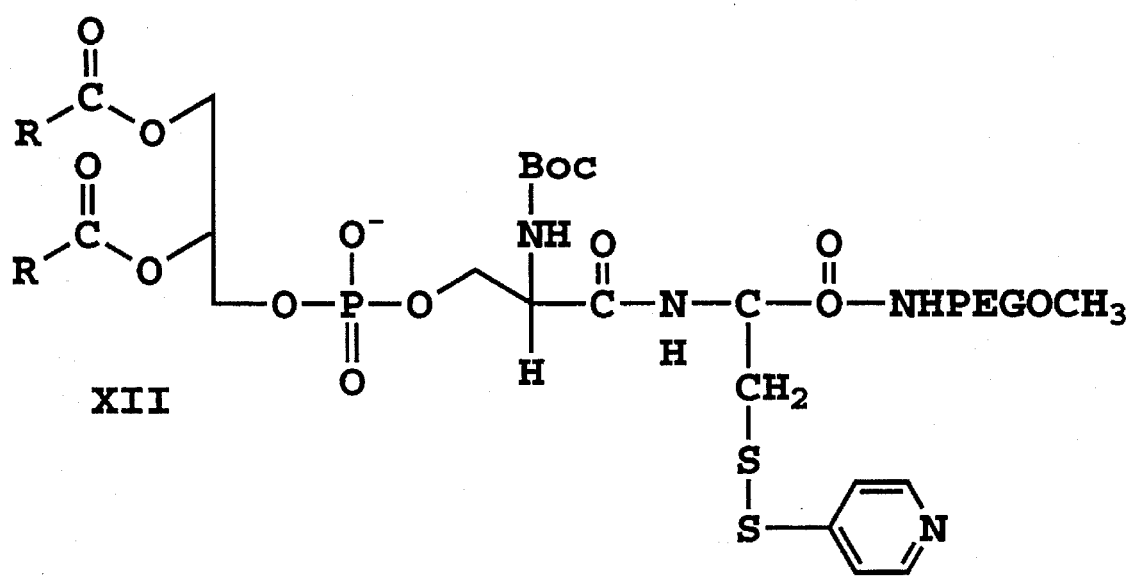
1) DTT
2) H+
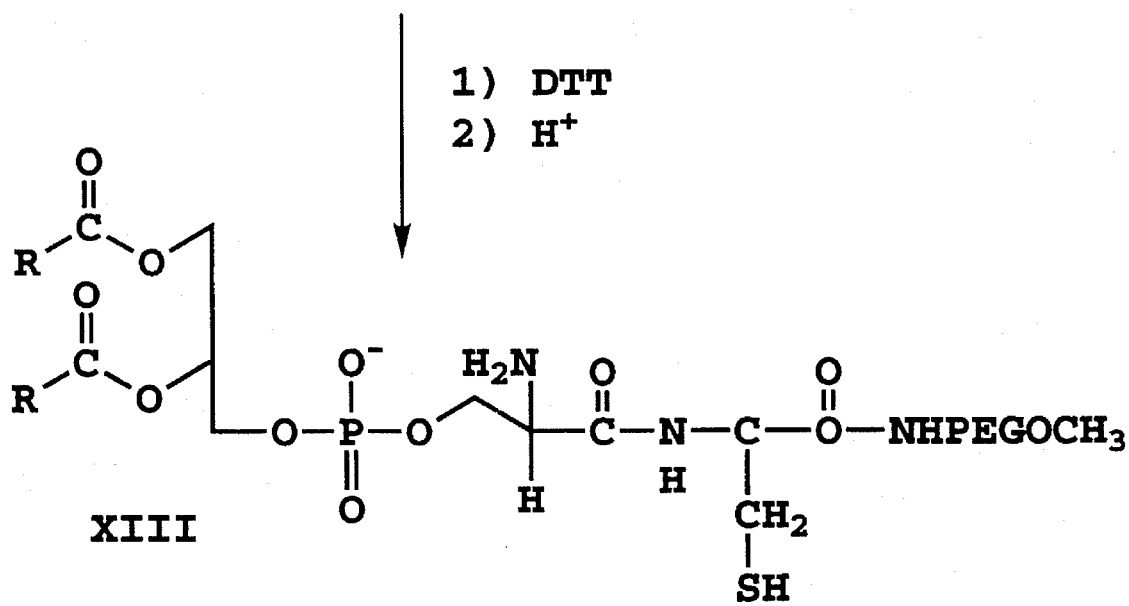
Fig. 5B

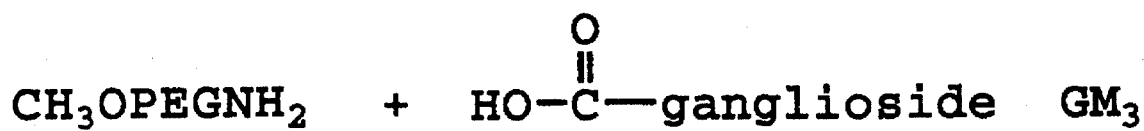
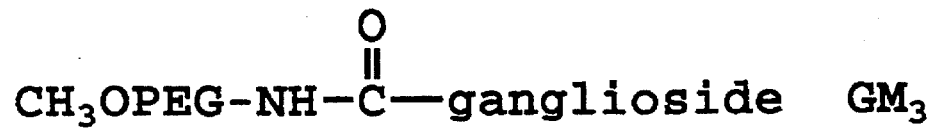
Fig. 7

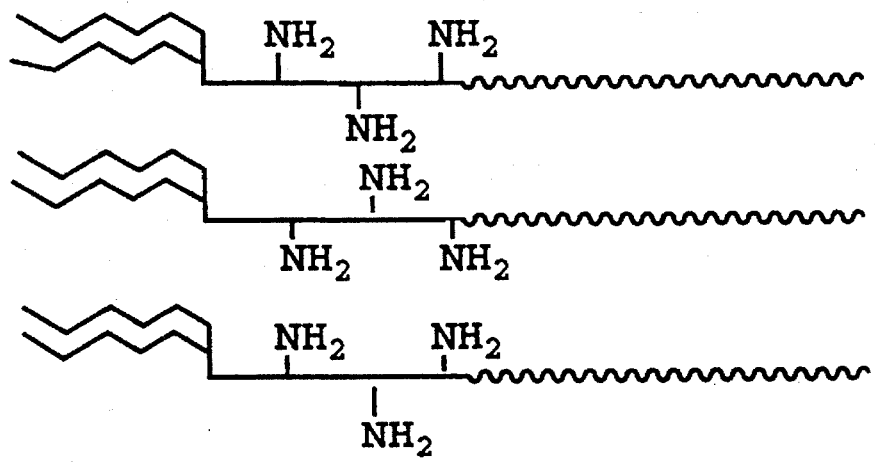
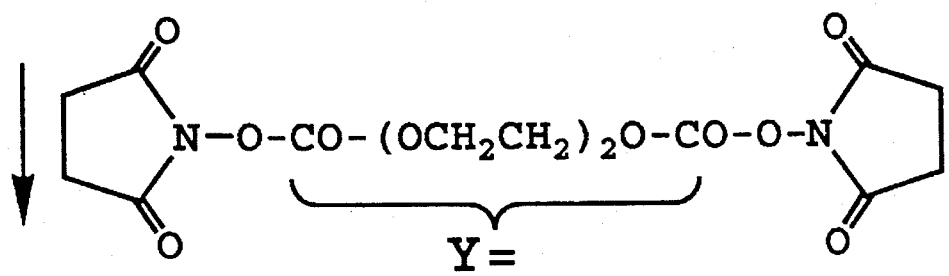
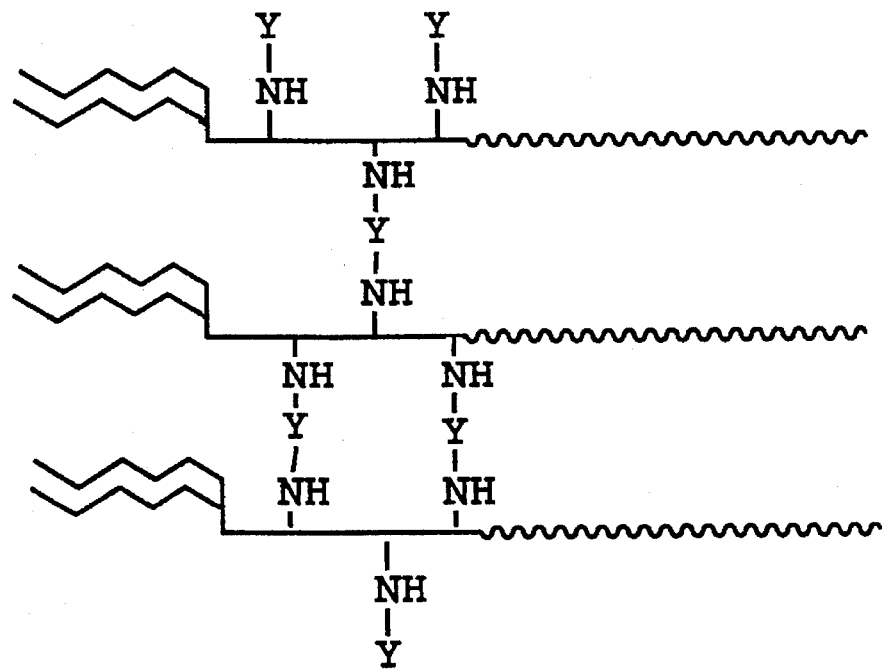
Fig. 14

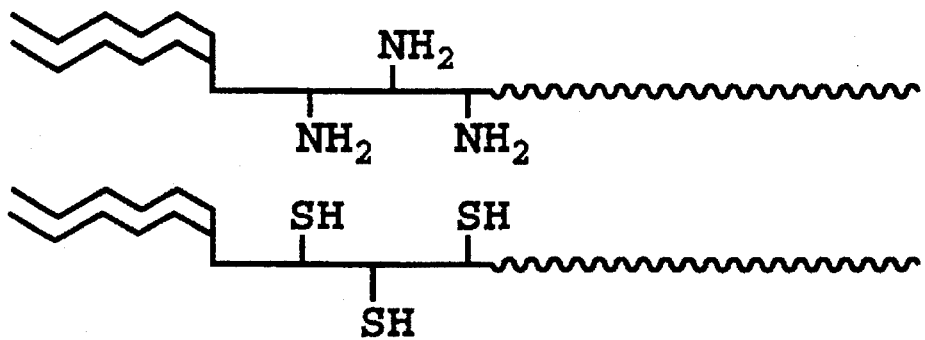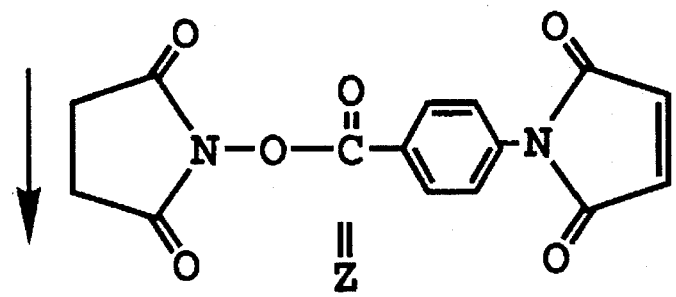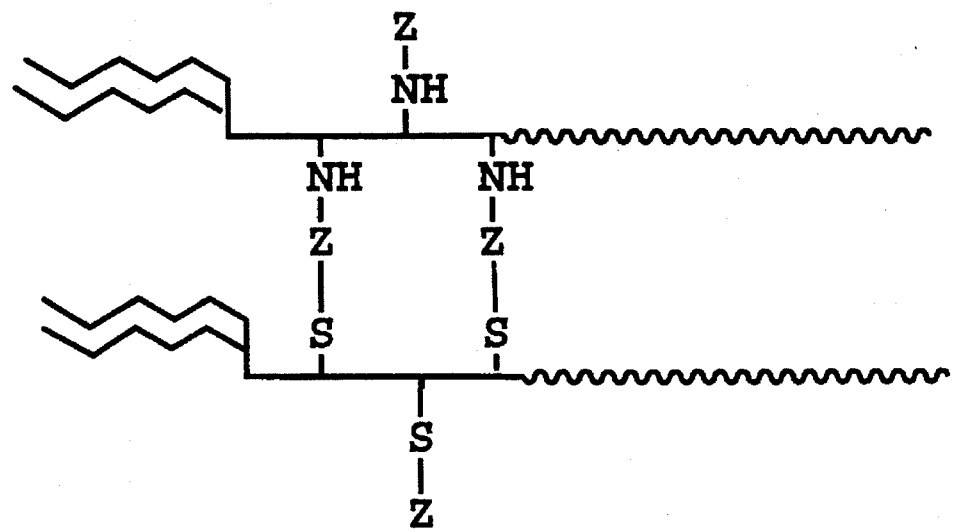
Fig. 16

POLYMER COMPOUND AND COATED PARTICLE COMPOSITION

FIELD OF THE INVENTION

The present invention relates to a polymer compound, a pharmaceutical composition employing the compound, and to methods of forming the pharmaceutical composition.

REFERENCES

Anderson, G. W., et al., (1964) J. Amer. Chem. Soc. 86:1839.
Bodanszky, M., *Principles of Peptide Synthesis* (1984) Springer-Verlang, Berlin.
Bohak, Z., and Katchalski, E. (1963) Biochemistry 2:227–238.
Bobbit, J. M. (1956) Adv. Carbohyd. Chem. 11:1.
Domb, A. J. (1990) Biomaterials 11:686–689.
Hofmann, K., et al., (1960) J. Amer. Chem. Soc. 82:3727–3732.
Ito, Y. (1992) Biotechnol. Lett. 14:1149–1152.
Jue, R, et al., (1978) Biochem. 17:5399.
Langer, R. S, and Peppas, N. A (1981) Biomaterials 2:201–214.
McCully, K. S., et al., (1990) Atherosclerosis 83:197–206.
MOSS, J., et al., (1977) Biochem. 16:1876–1881.
Otsu, T. (1992) Eur. Polym. J. 28:1325–1329.
Szoka, F., Jr., et al., (1980) Ann. Rev. Biophys. Bioeng. 9:467.
Wong, S. S., (1991) In: *Chemistry of Protein Conjugation and Cross-linking*, CRC Press.
Zalipsky, S. (1983) Eur. Polym. J. 19:1177.
Zalipsky, S. (1992) U.S. Pat. No. 5,122,614.

BACKGROUND OF THE INVENTION

Numerous pharmaceutical drug release systems exist for controlled delivery of drugs in the bloodstream. These systems have been developed to maintain drug levels within a therapeutically desirable range in the bloodstream, to protect drugs that have short in vivo half-lives, and to prevent harmful side effects resulting from drug administration at high doses. These pharmaceutical drug release systems may also allow less frequent drug administration (Langer).

An ideal system for drug delivery via the bloodstream would be capable of circulating for long periods in the bloodstream, would release an entrapped drug at a controlled rate, would have the potential to reach target sites via the bloodstream, and ultimately, would be cleared or broken down without release of toxic by-products.

SUMMARY OF THE INVENTION

The invention includes, in one aspect, a pharmaceutical particle composition for use in parenteral administration of a pharmaceutical compound. The particles have a selected uniform size in a size range less than 1 micron. Each particle is composed of a layer of linked polymer compounds, where each linked polymer compound includes (i) an exterior hydrophilic polymer, and (ii) an interior linking segment having at least two chemical groups which are crosslinked covalently to interior linking segments of two or more adjacent polymer compounds. The chemical groups of adjacent linked polymer compounds are crosslinked by a crosslinking structure to form a crosslinked particle surface coated by the exterior hydrophilic polymers. The particles contain an entrapped pharmaceutical compound.

In one embodiment of the invention, the crosslinking structure includes disulfide or thioether linkages linking sulfhydryl chemical groups in the linking segments of adjacent linked polymer compounds.

In another embodiment, the crosslinking structure includes carbon-carbon bonds derived from vinyl group polymerization initiated from a radical initiator attached to the particle surface.

In another embodiment, the crosslinking structure includes amide linkages linking amine chemical groups in the linking segments of adjacent linked polymer compounds. Alternatively, the crosslinking structure includes both amide linkages and disulfide or thioether linkages.

In still another embodiment, the linked polymer compounds making up the particles include a mixture of linked polymers having different chemical groups, in non-crosslinked form, and the crosslinking structure crosslinks the different chemical groups on adjacent linked polymer compounds.

In another aspect, the invention includes an amphipathic polymer compound. In one embodiment the compound consists of a hydrophilic polymer, a hydrophobic moiety, and a linking segment linking the polymer to the hydrophobic moiety and containing at least two chemical groups by which the compound can be crosslinked to two or more adjacent amphipathic polymer compounds. In another embodiment the compound contains a glycolipid having multiple hydroxyl groups. The glycolipid serves as the linking segment and hydrophobic moiety, and the hydrophilic polymer is attached covalently to the glycolipid.

The hydrophilic polymer is preferably polyethylene glycol, and the hydrophobic moiety is preferably a vesicle-forming lipid moiety. The vesicle-forming lipid moiety may be, for example, a phospholipid whose polar head group is covalently attached to the linking segment, a sterol covalently attached to a linking segment by a sterol hydroxyl group, or a hydrocarbon chain covalently attached to a linking segment through a suitable reactive group at one end of the chain.

The chemical groups on the linking segment are preferably amine, sulfhydryl, or vinyl groups, but may be other reactive groups, such as aldehyde, carboxylic acid or hydroxyl groups.

Also disclosed is a method for preparing a pharmaceutical composition composed of particles having a selected uniform size in a size range less than 1 micron and a surface coating of hydrophilic polymers, for parenteral administration of a particle-entrapped pharmaceutical compound. The method includes the steps of preparing, in an aqueous medium, lipid structures containing an ordered array of molecules of the polymer compound, and crosslinking the chemical groups in the linking segments of the polymer compounds.

In one embodiment the lipid structures are vesicular lipid structures prepared by suspending in an aqueous medium, a mixture of between 1–30 mole percent of the polymer compound and between 70–99 mole percent vesicle-forming lipids and a pharmaceutical compound, and sizing the structures to the uniform selected particle size. After crosslinking, the vesicle-forming lipids may be removed, e.g., by exposing the crosslinked particles to a detergent of water-miscible solvent, such as ethanol.

In another embodiment the lipid structures are micellar structures prepared by suspending the polymer compound in an aqueous medium at a concentration above the critical micelle concentration of the polymer compounds.

These and other objects and features of the invention will become more fully apparent when the following detailed description of the invention is read in conjunction with the accompanying drawings.

BRIEF DESCRIPTION OF THE DRAWINGS

FIG. 1 illustrates a polymer compound formed in accordance with the invention;

FIGS. 2A through 2D illustrate specific embodiments of exemplary polymer compounds formed in accordance with the invention;

FIGS. 5A–5B show a method of forming a polymer compound including PEG, a linking segment containing a sulfhydryl group, and a phospholipid that contributes an amine group to the linking segment;

FIG. 7 shows a method of forming a polymer compound including PEG and ganglioside $G_{M3}$, where the sugar residues of the sphingolipid serve as the linking segment;

FIG. 14 illustrates a step in forming crosslinking structures between adjacent polymer compounds whose linking segments contain amine groups;

FIG. 15A shows the preparation of a radical initiator compound, and FIG. 15B shows crosslinking structure formation; and FIG. 16 illustrates a step in forming crosslinking structures between adjacent first and second polymer compounds whose linking segments contain amine and sulfhydryl groups, respectively.

DETAILED DESCRIPTION OF THE INVENTION

I. Definitions

Figure 3:
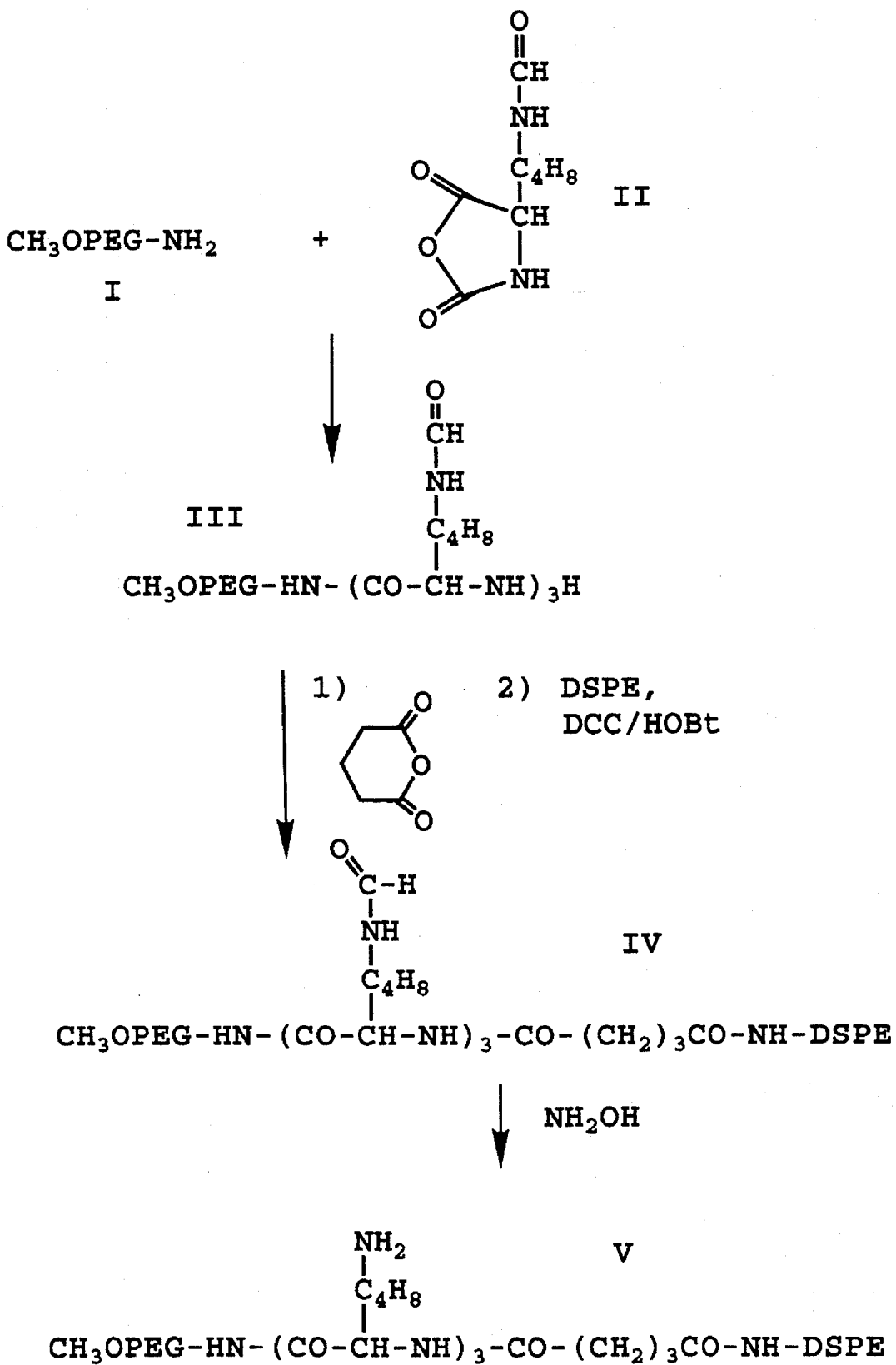
FIG. 3 shows a method of forming a polymer compound including polyethylene glycol (PEG), a polylysine linking segment, and a phospholipid.

"Vesicle-forming lipid" refers to any amphipathic lipid having hydrophobic and polar head group moieties, and which (a) can form spontaneously into bilayer vesicles in water, as exemplified by phospholipids, or (b) is stably incorporated into lipid bilayers, with its hydrophobic moiety in contact with the interior, hydrophobic region of the bilayer membrane, and its polar head group moiety oriented toward the exterior, polar surface of the membrane.

A "linkage" between two chemical groups on adjacent molecules refers to the molecular chain which serves to link the two chemical groups. The linkage may be a direct linkage, such as a disulfide bond formed between two sulfhydryl groups, or may involve a bridge linking the two chemical groups. The linkage may be defined in terms of one or both bonds involving the two linked chemical groups. Thus, for example, a "disulfide linkage" is formed by oxidation of two sulfhydryl chemical groups.

"Glycolipid" refers to an amphipathic lipid having sugar residues at its polar head group moiety. For purposes of this invention, glycolipids include phospholipids, such as phosphatidylinositol, and sphingolipids such as gangliosides.

II. Polymer Compound

FIG. 1 illustrates an exemplary polymer compound 14 formed in accordance with the invention. The compound includes a hydrophilic polymer 16, a hydrophobic moiety 18, and a linking segment 20 linking the polymer to the hydrophobic moiety and having at least two chemical groups, such as chemical groups 22, by which the compound can be crosslinked to at least two other polymer compounds.

In a preferred embodiment, the hydrophilic polymer is a polyethylene glycol (PEG) chain with a molecular weight of between 1,000 to 5,000 daltons. Typically, the PEG chain has a molecular weight of about 2,000 and contains an unreactive methoxy group at its free end, and is coupled to the linking segment through a reactive chemical group, as will be described below.

Alternative hydrophilic polymers include, but are not limited to, polylactic acid, polyglycolic acid, polyvinylpyrrolidone, polymethacrylamide, polyethyloxazoline, polymethyloxazoline, or polydimethylacrylamide. As described above for PEG, each of these hydrophilic polymers preferably has an unreactive group at its free end, and is coupled to the linking segment through a reactive chemical group.

The hydrophobic moiety is a vesicle-forming lipid, such as a phospholipid, a glycolipid, a sterol or a fatty acid. The hydrophobic moiety used for forming the polymer compound contains a chemical group at its polar head group suitable for linking to a linking segment. The polar head group may contain, for example, an amine group, hydroxyl group, aldehyde group or a carboxylic acid group.

Additionally, the hydrophobic moiety is selected to form lipid structures in an aqueous medium. These lipid structures may be either vesicular or core lipid structures. The hydrophobic moiety is selected to achieve a specified degree of fluidity or rigidity of a lipid structure, and to control the stability of lipid structures in an aqueous solution.

One class of preferred hydrophobic moieties includes lipids having two hydrocarbon chains. Included in this class are phospholipids, such as phosphatidylcholine (PC), phosphatidylethanolamine (PE), phosphatidic acid (PA), phosphatidylglycerol (PG), phosphatidylinositol (PI), and glycolipids, such as sphingomyelin (SM), where the two hydrocarbon chains are typically between about 14–22 carbon atoms in length, and may contain unsaturated carbon-carbon bonds.

The linking segment links the hydrophilic polymer to the hydrophobic moiety and contains at least two chemical groups which can be reacted with chemical groups of adjacent polymer compounds and which can form part of a crosslinking structure, as described below. Chemical groups of the linking segment may be amine, sulfhydryl, vinyl, hydroxyl, carboxyl, or aldehyde groups.

In one embodiment the linking segment can contain two chemical groups for crosslinking two neighboring polymer compounds as will be described below. In another preferred embodiment, the linking segment contains more than two chemical groups for crosslinking several neighboring polymer compounds. The chemical groups on any particular linking segment may be identical or may be different groups.

In a further embodiment the linking segment is formed, partially or completely, by the polar head group of the hydrophobic moiety, such as will be illustrated below with respect to FIG. 2C.

FIGS. 2A through 2D illustrate three embodiments of polymer compounds formed in accordance with the invention. FIG. 2A illustrates a polymer compound containing a polyethylene glycol (PEG) hydrophilic polymer, a distearylphosphatidylethanolamine (DSPE) hydrophobic moiety, and a linking segment containing three free amino groups.

FIG. 2B illustrates a polymer compound containing a polyethylene glycol (PEG) hydrophilic polymer, a distearylphosphatidylethanolamine (DSPE) hydrophobic moiety, and a linking segment containing an amine and a sulfhydryl group.

FIG. 2C illustrates a polymer compound containing a polyethylene glycol (PEG) hydrophilic polymer and a hydrophobic moiety and a linking segment formed by the inositol moiety of phosphatidylinositol. The lipid and linking segment may be formed of other glycolipids, such as ganglioside lipids, as exemplified by $GM_1$.

FIG. 2D illustrates a polymer compound containing a polyethylene glycol (PEG) hydrophilic polymer, a distearylphosphatidylethanolamine (DSPE) hydrophobic moiety, and a linking segment containing a vinyl group.

A. Polymer Compound preparation. The polymer compound of the invention is typically prepared by first forming a hydrophilic polymer having the linking segment attached at one polymer end, then attaching the free end of the linking segment to a suitable lipid which will form the hydrophobic moiety in the compound.

Alternatively, the polymer compound may be prepared by first linking a lipid to a linking segment, then attaching the available free end of the linking segment to a hydrophilic polymer.

In still another embodiment, the linking segment is formed by joining a hydrophilic polymer (which may contain a portion of the linking segment) to a lipid, which will provide a portion or all of the linking segment, such as indicated above. Various methods of compound preparation will be appreciated from the reaction schemes illustrated in FIGS. 3–10.

FIG. 3 shows a method of forming a polymer compound like the one shown in FIG. 2A. The free hydrophilic polymer is monoamine PEG (compound I). The precursor of the linking segment is an N-carboxyanhydride of lysine which is protected at its epsilon-amine group by a formyl group (compound II). Reaction of an amine group of a PEG chain opens the ring of the N-carboxyanhydride, yielding a free amine group, followed by propagation of an NCA ring-opening polymerization reaction (Bohak), to yield compound III having a PEG polymer and a (protected-lysyl)$_3$ linking segment.

To form the polymer compound, a lipid such as DSPE is linked to the free end of the linking segment. This is done in the present example, by reacting compound III first with glutaric anhydride, followed by coupling with DSPE in the presence of dicyclohexylcarbodiimide (DCC) and 1-hydroxybenzotriazole (HOBt) to form compound IV. In another method to form the polymer compound, a bifunctional reagent can be used to couple the hydrophobic moiety to the linking segment, such as by use of excess disuccinimidyl suberate, followed by reaction with DSPE.

The formyl protecting groups on lysine are removed by reaction with 5% aqueous hydrazine acetate or hydroxylamine hydrochloride in pyridine to form compound V (Hofmann). Details of the polymer compound preparation are given in Example 1.

Figure 4:
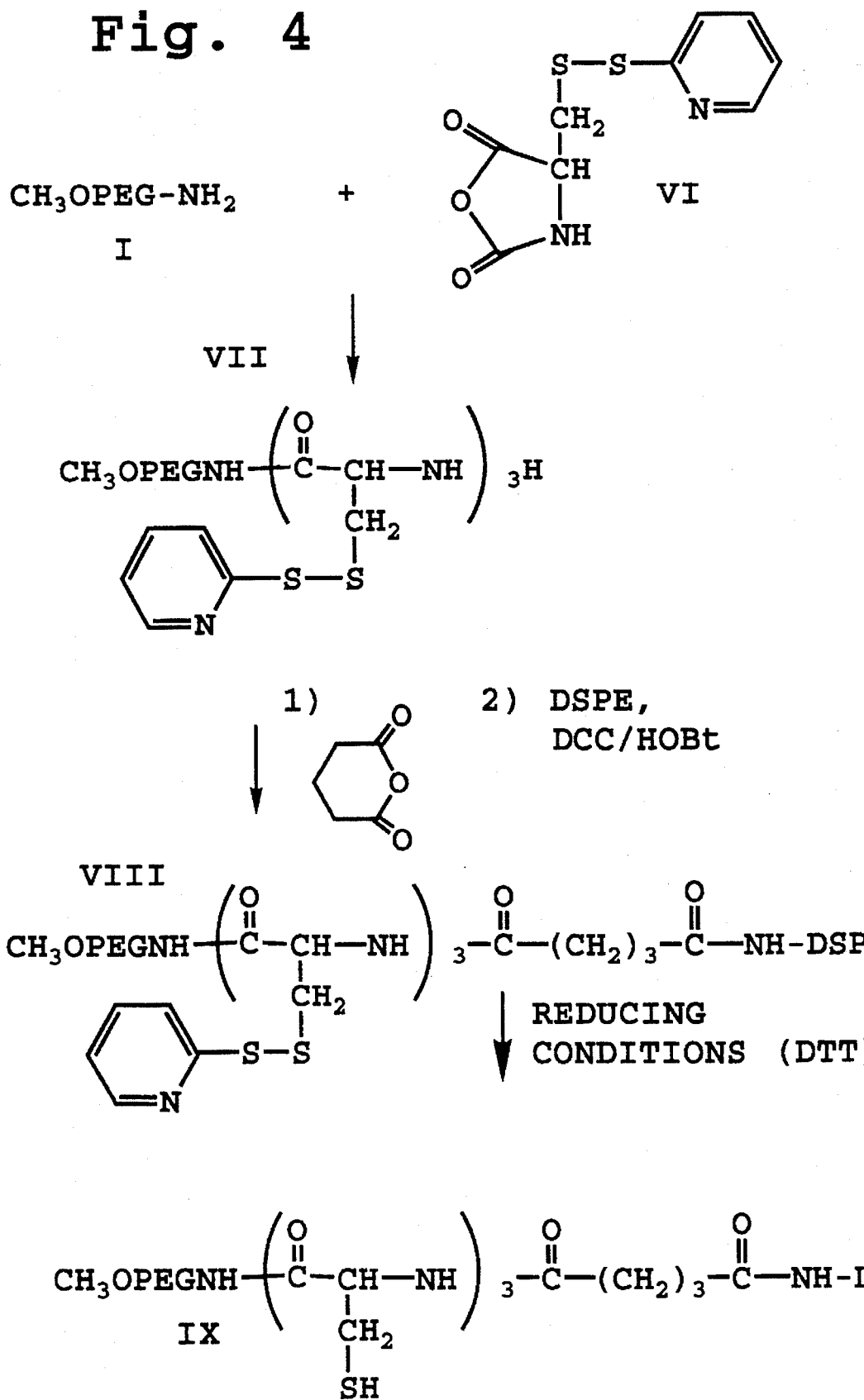
FIG. 4 shows a method of forming a polymer compound including PEG, a polycysteine linking segment, and a phospholipid.

FIG. 4 shows a method of forming a polymer compound containing multiple sulfhydryl groups derived from cysteine. The free hydrophilic polymer is monoamine PEG (compound I). The precursor of the linking segment is an N-carboxyanhydride of cysteine which is protected at its sulfhydryl group by a thiopyridine group (compound VI). Reaction of an amine group of the PEG chain opens the ring of the N-carboxyanhydride, as illustrated in FIG. 4, to form compound VII.

To form the polymer compound, a lipid such as DSPE is linked to the free end of the linking segment. This is done in the present example, by reacting compound VII first with glutaric anhydride, followed by coupling with DSPE in the presence of dicyclohexylcarbodiimide (DCC) and 1-hydroxybenzotriazole (HOBt) to form compound VIII. The thiopyridine groups are removed under reducing conditions to form product (compound IX). Polymer compound preparation is described in Example 2.

Figure 5A:
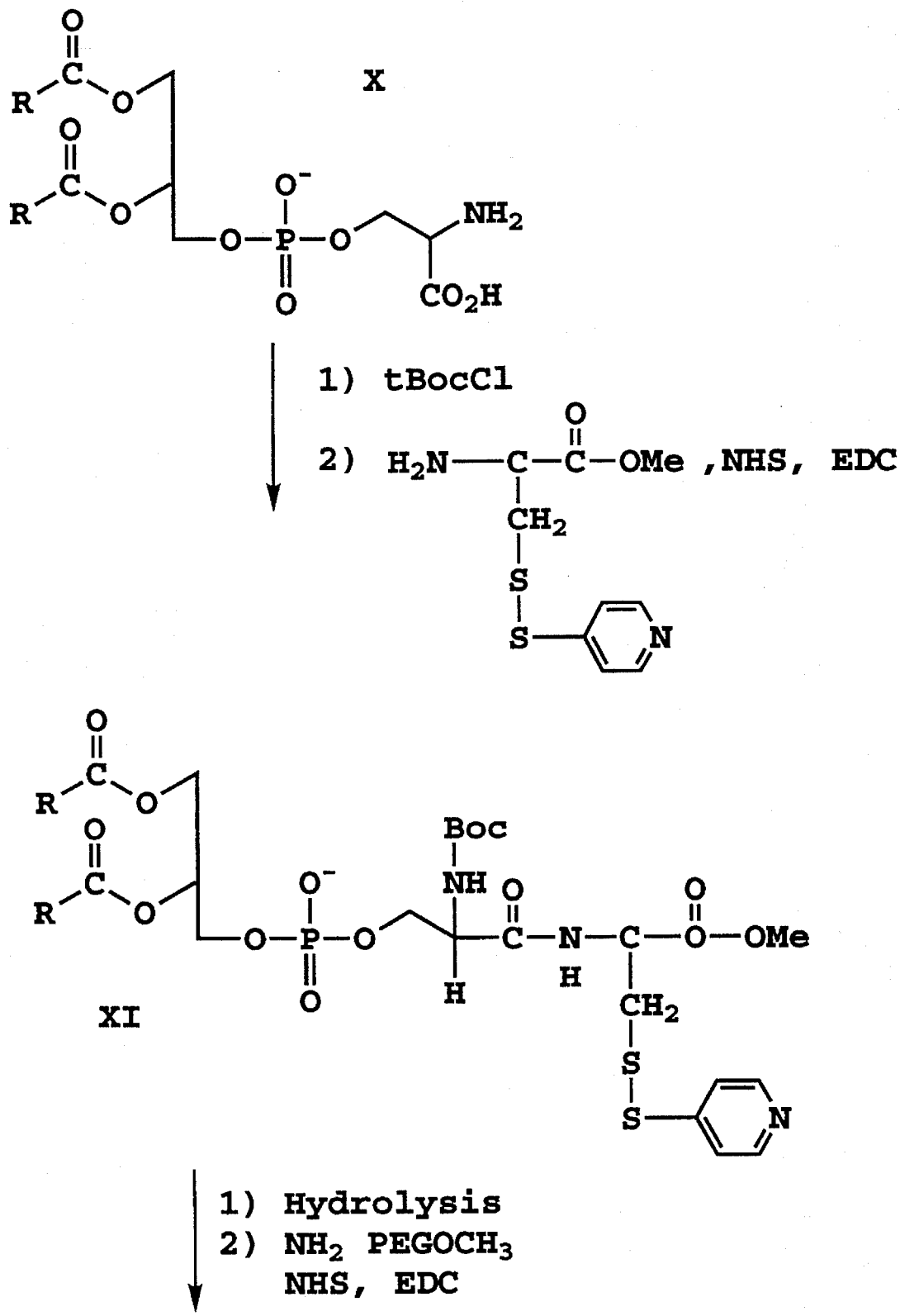

FIGS. 5A–5B show a method of preparing a polymer compound, containing amine and sulfhydryl groups. In this example the amine group of phosphatidylserine (compound X) is protected by reaction with t-butoxycarbonyl chloride to form t-butoxycarbonyl-N-phosphatidylserine. This compound is condensed by the N-hydroxysuccinimide method with a cysteine methylester whose free sulfhydryl group is protected by 4-thiopyridine to form compound XI (Anderson). Then the methyl ester group is hydrolyzed, and compound XI is condensed with PEG monoamine (compound I) to form compound XII. The protecting groups are removed to form polymer compound (compound XIII).

Figure 6:
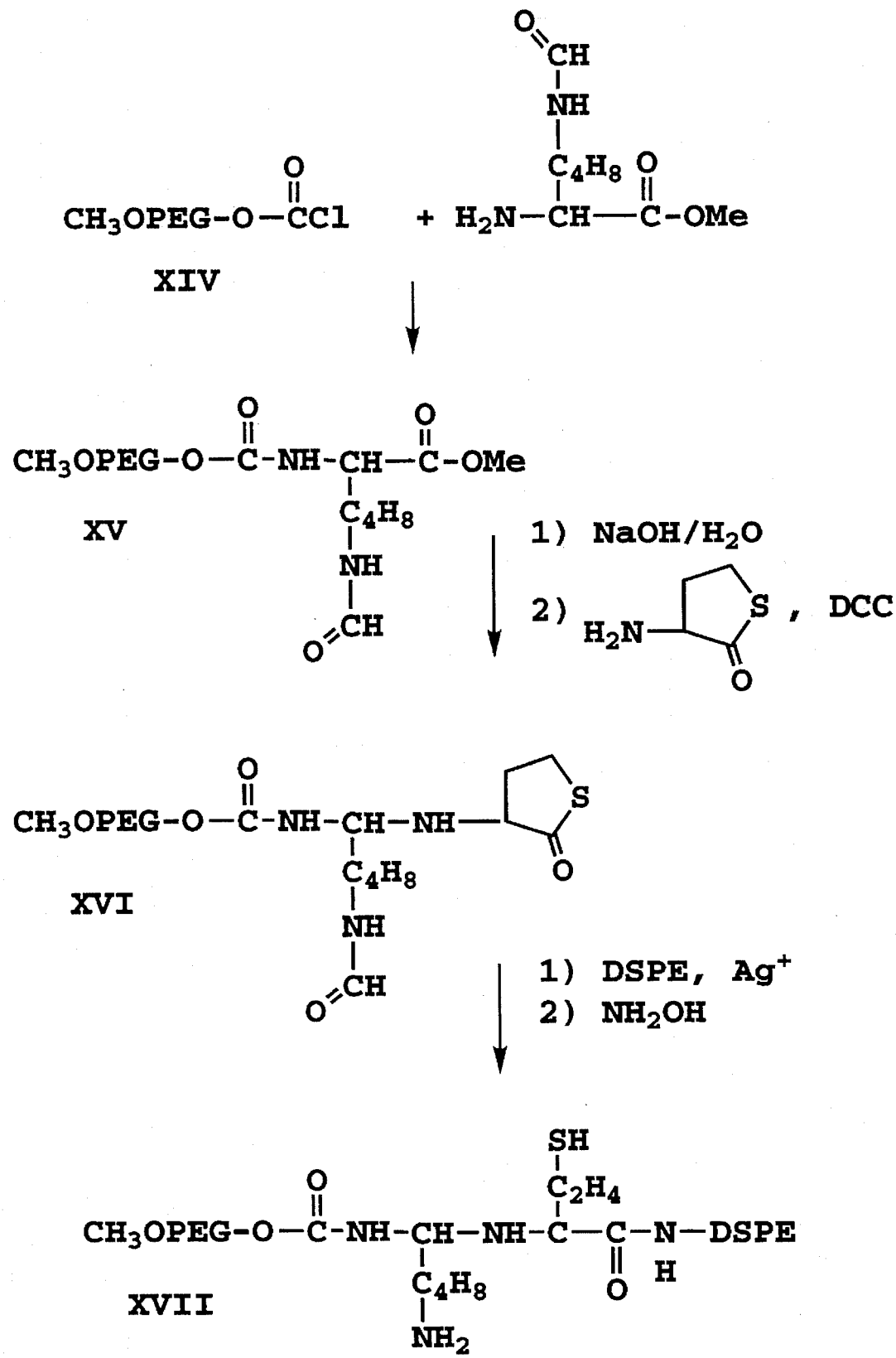
FIG. 6 shows another method of forming a polymer compound including PEG, a linking segment containing a sulfhydryl group and an amine group, and a phospholipid.

FIG. 6 shows a method of preparing another polymer compound containing two different chemical groups in the linking segment as shown in FIG. 2B. PEG containing a terminal chloroformate group (compound XIV) obtained from PEG mono alcohol reaction with phosgene is reacted with N-formyl lysine methyl ester to form a PEG derivative containing a formyl-group protected amine group and a methyl ester group (compound XV) (Hofmann). The methyl ester group is hydrolyzed to its corresponding carboxylic acid group prior to reaction with homocysteine thiolactone to form a polymer derivative containing a terminal thiolactone ring (compound XVI) (McCully). Upon reaction with a vesicle-forming lipid, such as DSPE, in the presence of silver ion at a neutral pH the thiolactone ring is opened and a free sulfhydryl group is generated. The formyl protecting groups on lysine are removed as has been described above. In this manner a polymer compound (compound XVII) is generated which contains both an amine and a sulfhydryl group. Polymer compound preparation is described in Example 3.

FIG. 7 shows a method of preparing a polymer compound of the type shown in FIG. 2C. The compound is prepared by coupling PEG having a terminal amine group (compound I) to ganglioside $G_{M3}$. The single carboxylic acid group of the sialic acid sugar residue is activated with N-hydroxysuccinimide in the presence of EDC, and reacted with PEG, to form compound XVIII.

Similarly, a phospholipid, such as phosphatidylinositol (PI), may be coupled to a hydrophilic polymer with a terminal amine group by an initial mild periodate oxidation step, followed by reductive amination. Alternatively, a PEG-PI polymer compound may be obtained by esterification of PI with a mono carboxylic acid derivative of PEG.

Figure 8:
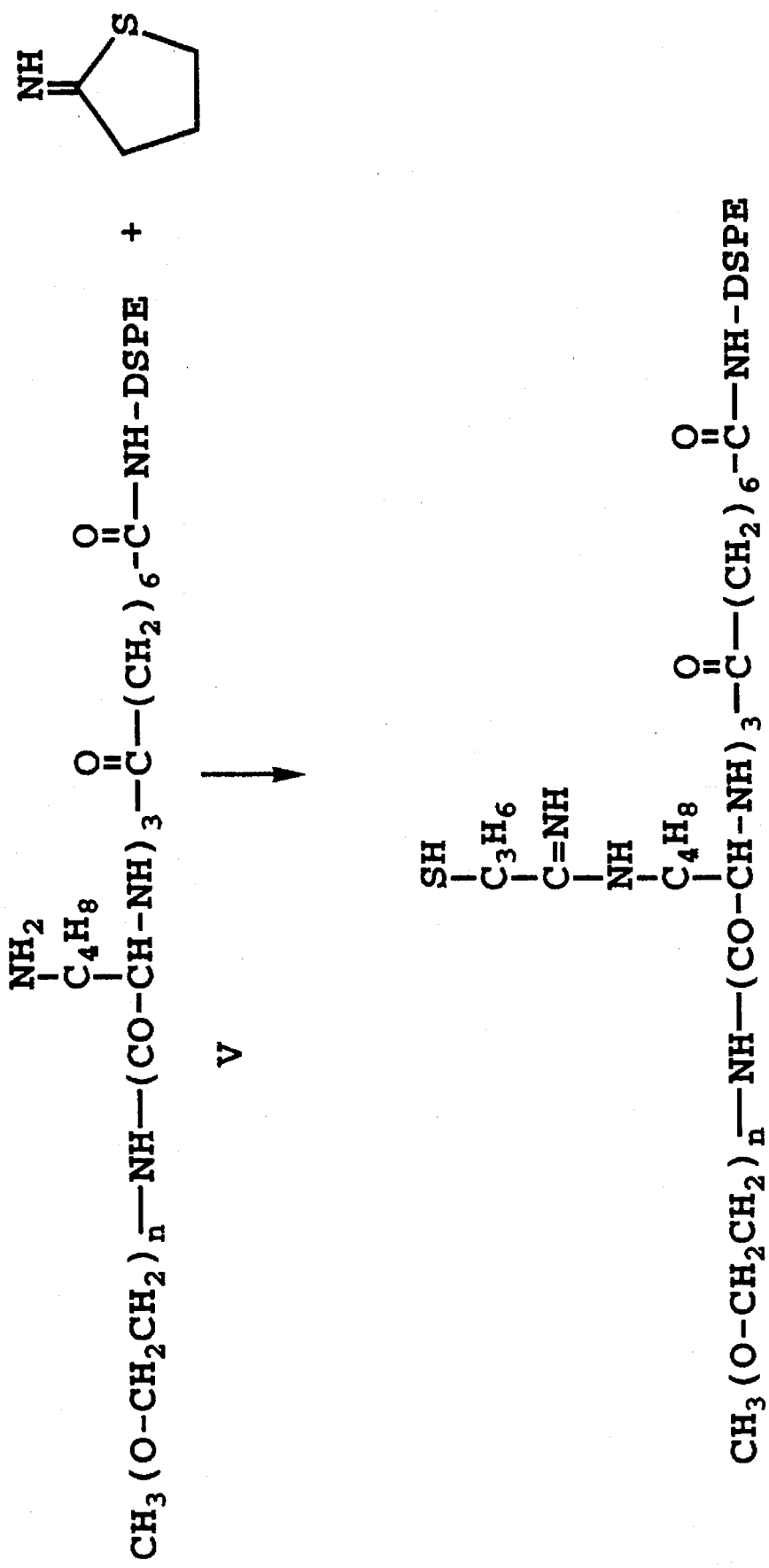
FIG. 8 illustrates a method of modifying a polymer compound having free amine groups in its linking segment to one having sulfhydryl groups in its linking segment.

FIG. 8 illustrates how a polymer compound of the type shown in FIG. 2A, i.e., one having free amine groups in its linking segment (compound V), can be modified to contain sulfhydryl groups in the linking segment. Here the polymer compound containing amine chemical groups (compound V) is reacted with Traut's reagent (2-iminothiolane) (Jue), to convert the amine groups to sulfhydryl groups as indicated (compound XIX).

Figure 9:
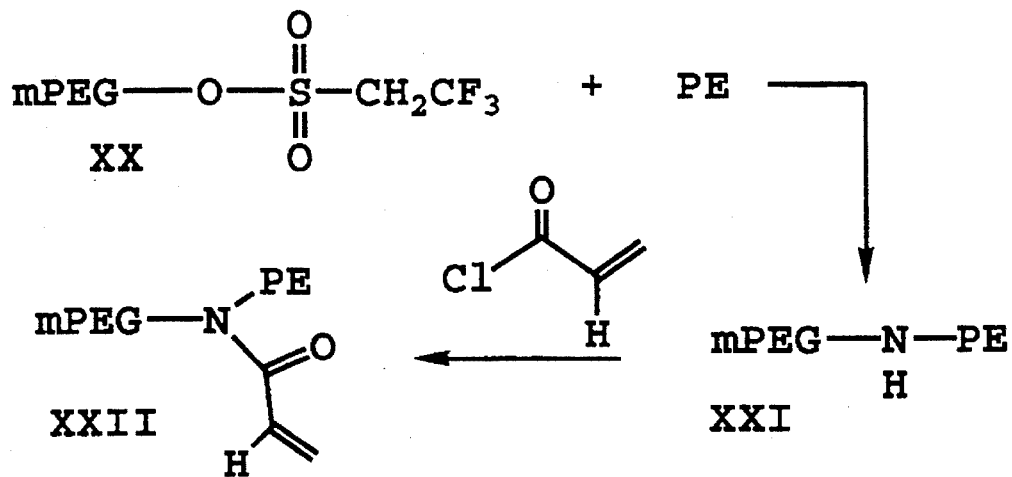
FIG. 9 illustrates a method of forming a polymer compound including PEG, a linking segment containing a vinyl group, and a phosphatidylethanolamine lipid.

FIG. 9 illustrates how vinyl groups may be included in a polymer compound to generate a polymer compound of the type shown in FIG. 2D. The hydrophilic polymer is monomethoxy PEG which is reacted with the anhydride of trifluoroethyl sulfonyl chloride to activate the free PEG end (compound XX). Reaction of the activated compound with a lipid amine, such as PE, in the presence of triethylamine, gives the PE-PEG derivative (compound XXI). Compound XXI is reacted with acryloyl chloride in the presence of triethylamine to form desired product. Compound XXI PEG-lipid derivative containing secondary amino group can also react with other vinylic compounds, such as methacryloyl chloride, to form a related product. Reaction procedures are described in Example 4.

Figure 10:
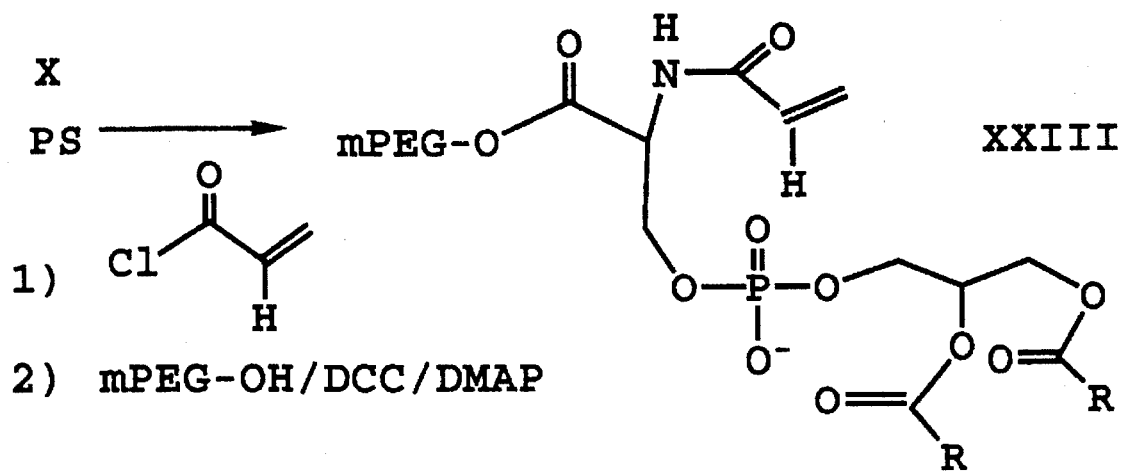
FIG. 10 illustrates a method of forming a polymer compound including PEG, a linking segment containing a vinyl group, and a phosphatidylserine lipid.

FIG. 10 illustrates another reaction scheme for incorporating vinyl groups in a polymer compound. In this example the amine group of phosphatidylserine (PS) (compound X) is reacted with acryloyl chloride. The phosphatidylserine carboxyl group is then activated by reaction with dicyclohexylcarbodiimide and 4-dimethylaminopyridine (DMAP) for condensation with monomethoxy PEG to form compound XXIII (Zalipsky, 1983). It will be appreciated from the above how polymer compounds composed of a variety of hydrophilic polymers, linking segments, and hydrophobic moieties can be prepared.

III. Pharmaceutical Composition

In another aspect, the invention includes a pharmaceutical composition containing particles of a selected uniform size with a particle-entrapped pharmaceutical compound. The particles in the composition are each composed of a single layer of linked polymer compounds, where each linked polymer compound includes (i) an exterior hydrophilic polymer, and (ii) an interior linking segment having at least two chemical groups which are crosslinked covalently to interior linking segments of two or more adjacent polymer compounds. The crosslinked chemical groups form part of crosslinking structures creating a crosslinked particle surface which is coated by the hydrophilic polymers of the linked polymer compounds.

Figure 11:
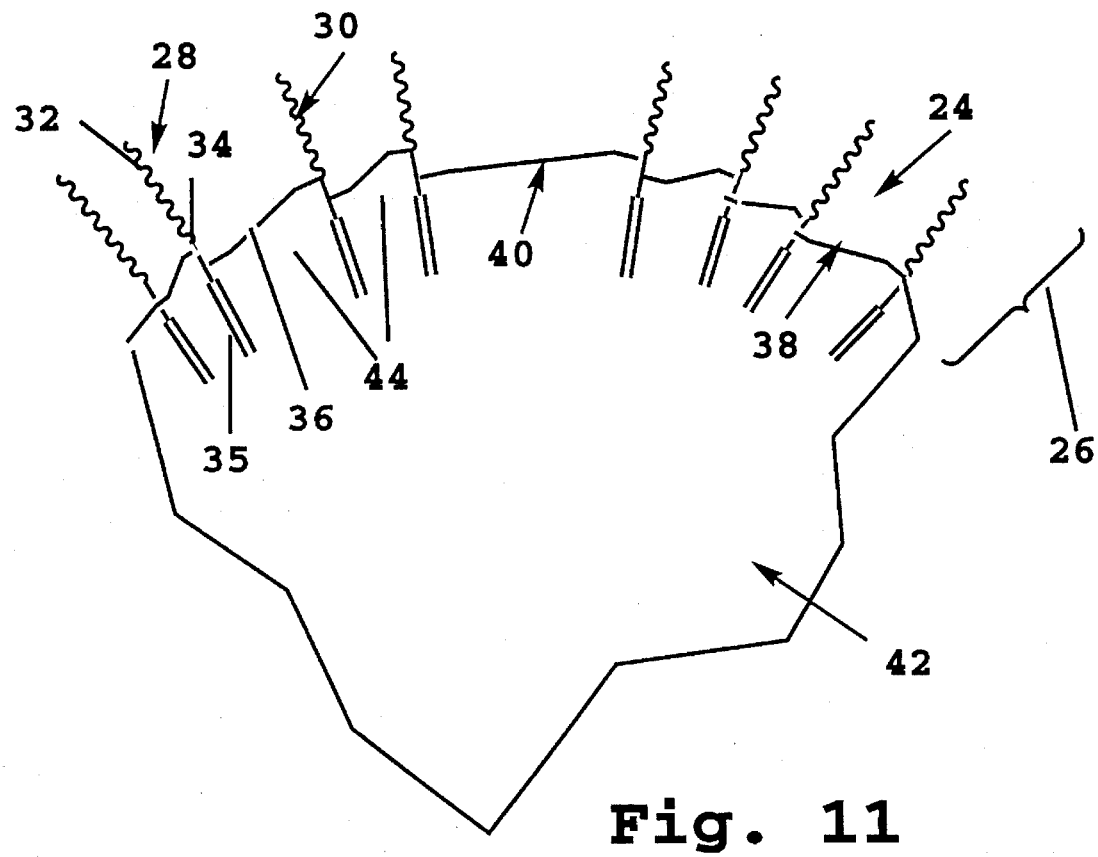
FIG. 11 shows, in schematic view, a cross-sectional slice of a particle formed in accordance with one embodiment of the invention.

A. Vesicular Particles. In one general embodiment, the particles forming the composition are vesicular particles having an aqueous interior, and an outer polymer coating. FIG. 11 shows, in schematic view, a cross-sectional slice of a particle 24 formed in accordance with this embodiment of the invention. The particle is composed of a single layer 26 of linked polymers, such as linked polymers 28, 30, each having an exterior hydrophilic polymer, such as polymer 32, and an interior linking segment, such as segment 34, in linked polymer 28. In this vesicular-structure embodiment, the polymer compounds also contain a hydrophobic moiety, such as a diacylchain moiety (indicated at 35 in compound 28). Such polymer compounds are formed as described in Section II.

As described in Section II, each linking segment in a linked polymer compound has at least two chemical groups. Adjacent linked polymer compounds in the composition are linked together by linkages, such as linkage 36 between chemical groups in adjacent linked polymer compounds, such as adjacent polymers 28, 30. The adjacent linked compounds may be directly adjacent, or separated from one another by one or more polymer compounds or vesicle-forming lipids. Methods of forming the linkages between adjacent linked polymers will be described below.

The linkages between the linked polymer compounds are also referred to herein as a crosslinking structure. As will be seen below, this structure may include a direct chemical linkage, such as a disulfide bond, between the chemical groups of adjacent polymer compounds, or may include a chain or branched structure, such as formed by coupling two chemical groups with a bifunctional or multifunctional crosslinking reagent. The crosslinking structure, together with the linking segments of the polymer compounds, form a crosslinked particle surface 40 which is coated by the hydrophilic polymers, such as polymer 32, of the linked polymer compounds. The particle surface defines an aqueous interior volume 42 in the particle. As can be appreciated from FIG. 11, the particle surface has pores, such as pores 44, through which solute molecules may diffuse into and out of the particle's interior volume. The sizes of the pores can be selectively varied according to the extent of crosslinking in the polymer compounds. The particles also include a pharmaceutical or imaging agent, which may be entrapped in the interior region of the particles, or attached, e.g., by covalent attachment, to the particle surface or polymer coating. Methods for entrapping compounds in the particles will be considered below. The particles may also be designed, e.g., by covalent attachment of target-specific antigens to the polymer moieties, for particle targeting to specific sites, such as solid tumor sites.

Figure 12:
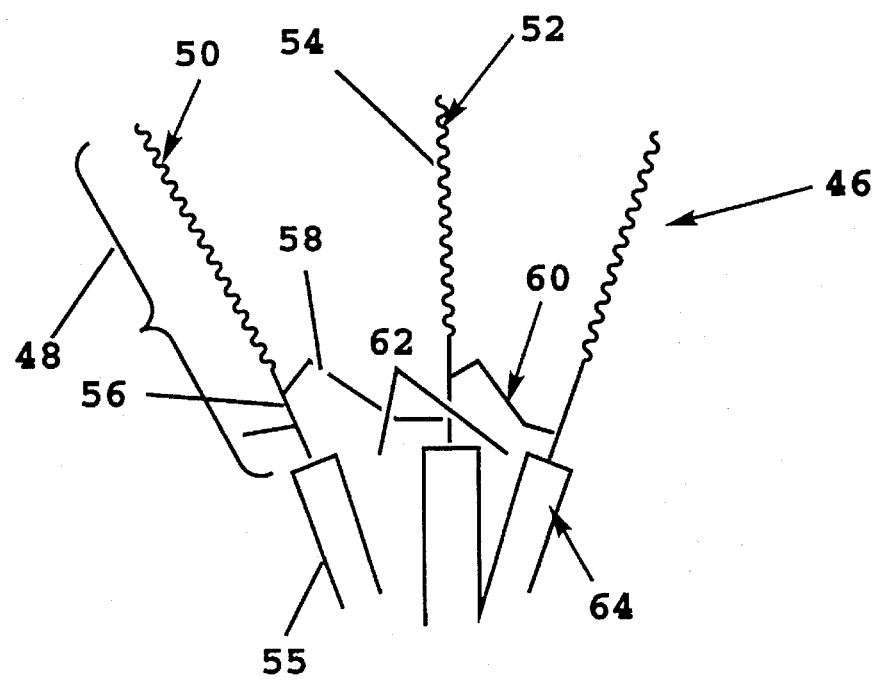
FIG. 12 shows, in schematic view, a cross-sectional slice of a particle formed in accordance with another embodiment of the invention.

B. Core Particles. In another embodiment, the particles forming the composition are core or micellar-like particles having a lipophilic interior region and a hydrophilic polymer coating. FIG. 12 shows, in schematic view, a cross-sectional slice of a particle 46 formed in accordance with this embodiment of the invention. The particle is composed of a single layer 48 of linked polymer compounds, such as compounds 50, 52, each having an exterior hydrophilic polymer, such as polymer 54, and an interior linking segment, such as segment 56, in linked polymer 50. As above, the polymer compounds forming the particle-core structures also contain a hydrophobic moiety, such as a diacyl-chain moiety (indicated at 55 in compound 50). Such polymer compounds are formed as described in Section II.

As described above, adjacent linked polymer compounds in the composition are linked together by linkages, such as linkage 58, between chemical groups in adjacent linked polymer compounds, such as adjacent polymers 50, 52, where the adjacent linked compounds may be directly adjacent, or separated from one another by one or more polymer compounds or vesicle-forming lipids. Methods of forming the linkages between adjacent linked polymers will be described below. The linkages, or crosslinking structures, form a particle surface 60, as described above, having pores, such as pores 62, through which drug compounds can diffuse from the hydrophobic interior 64 of the particle. The pore sizes can be selectively varied, as above.

The particles also include a pharmaceutical or imaging agent, which may be entrapped in the interior hydrophobic region of the particles, or attached, e.g., by covalent attachment, to the particle surface or polymer coating, and the particle may be designed for targeting, also as noted above.

As will be seen below, the core-structure particles can be formed by crosslinking micelles of the polymer compounds, or polymer compounds in combination with other micelie-forming surfactants. Similarly, the vesicular-structure particles can be formed by crosslinking lipid vesicles formed to include the polymer compounds in vesicle-forming lipids, such as phospholipids, alone or in combination with cholesterol.

IV. Particle Preparation

This section describes methods for preparing the vesicular and core particles described in the section above. For each particle type, a lipid structure having a selected uniform size and an ordered array of molecules of the polymer compound is first formed. The chemical groups of adjacent polymer compounds on the outer surface of such a lipid structure are then crosslinked. In the case of the vesicular particles, where vesicle-forming lipids are used to form the vesicles for crosslinking, the particles may be further treated to remove non-crosslinked lipids.

A. Preparing Non-Crosslinked Structures. Vesicular lipid structures used in forming vesicular particles are prepared from a mixture of polymer compound (described in Section II) and vesicle-forming lipids. The mole ratio of the polymer compound is typically between 1–30, preferably 5–15 mole percent, with the remainder being vesicle-forming lipids, such as phospholipids. More generally, vesicle-forming lipids may include a variety of amphipathic lipids having hydrophobic and polar head group moieties, and which (a) can form spontaneously into bilayer vesicles in water, as exemplified by phospholipids, or (b) is stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids are preferably ones having two hydrocarbon chains, typically acyl chains, and a polar head group. Included in this class are the phospholipids, such as phosphatidylcholine (PC), phosphatidylethanolamine (PE), phosphatidylglycerol (PG), phosphatidic acid (PA), phosphatidylinositol (PI), and sphingomyelin (SM), where the two hydrocarbon chains are typically between about 14–22 carbon atoms in length, and have varying degrees of unsaturation. Other suitable lipids include glycolipids and sterols, such as cholesterol.

The vesicular lipid structures can be formed by methods used conventionally for forming lipid vesicles, or liposomes. One standard method involves forming a lipid film, here composed of the polymer compound and vesicle-forming lipids, and hydrating the film with a suitable aqueous medium. Where the vesicles are designed to encapsulate a pharmaceutical agent, such as a peptide, the agent is preferably included in the hydration medium. Other vesicle-forming methods which are suitable include solvent injection and reverse-phase evaporation (Szoka). One advantage of the latter method is that the vesicle formed are largely unilamellar or oligolamellar.

After vesicle formation, the vesicles may be sized to a desired size less than 1 micron, using any of a variety of sizing methods. One preferred method involves extrusion through a polycarbonate membrane having a selected pore size, e.g., 0.08 to 0.5 microns, or by extrusion through other defined-pore membranes. This method generally produces vesicles having a selected average size corresponding to membrane pore size, and a narrow size distribution. Other vesicle-extrusion methods effective to produce vesicles having a selected size less than 1 micron are known. Alternatively, small, substantially homogeneous size vesicles may be formed by homogenization or sonication, according to well known methods.

In addition, the vesicles may be further treated, either before or after sizing, to remove non-encapsulated drug, where the drug is one which may be crosslinked to the vesicle surface by the crosslinking reaction used in crosslinking the polymer compounds in the vesicles. Drug removal may be, for example, by size exclusion chromatography.

The non-crosslinked structures used in forming the core or micellar particles described above are preferably micellar structures formed by suspending the polymer compound of Section II in an aqueous medium. Dispersion of polymer compounds may be facilitated by sonication or the like.

The micelles may additional include other micelie-forming lipids, such as fatty acids, or phospholipids, with the provision that the percentage of any vesicle-forming lipids in the composition is less than that which would lead to formation of lipid vesicles. One purpose of additional lipids in this embodiment is to control surface pore size, by varying the spacing between adjacent polymer compounds or between adjacent clusters of polymer compounds in the micelle. The size of the micelles is typically less than about 0.03 microns, and the micelle size is the approximate size that the crosslinked particles will have. Thus, the micellar particles will tend to be limited to defined small sizes, i.e., less than 0.03 microns.

The micelles may be additionally prepared to contain a pharmaceutical agent, preferably a lipophilic agent which can be retained in the hydrophobic interior of the particles. Non-bound agent can be removed, as above, prior to crosslinking.

It will be appreciated that the crosslinked particles of the invention may be made from other non-crosslinked structures having a defined size less than about 1 micron and coated with hydrophilic polymer molecules which can be crosslinked through chemical linking groups in a linking segment carried on each hydrophilic polymer.

As one example, polymer compounds containing a hydrophilic polymer and crosslinking segment are attached, through the chemical groups in the linking segments, to microparticles having surface reactive groups. Alternatively, polymer compounds additionally containing a hydrophobic moiety, such as described in Section II, are bound as a monolayer by hydrophobic interactions to the surface of hydrophobic microparticles having defined sizes in a selected size range less than 1 micron. Following crosslinking, the particles may be dissolvable in non-aqueous solvents or formed of a biodegradable material, such as polylactic acid or polyglycolic acid which can be removed in vivo.

To form the selected-size, crosslinked polymercoated particles of the invention, the non-crosslinked structures formed as above are treated to crosslink the chemical groups in the linking segments of the polymer compounds. As indicated above, the degree of crosslinking will determine the pore sizes of the particles, and can be varied according to (i) the mole percent of polymer compounds in the non-crosslinked structures, (ii) the number of chemical groups in the linking segments, and (iii) the extent of crosslinking among these groups. The latter factor, in turn, can be controlled by the type of crosslinking agent or nature of the crosslinking reaction, and the crosslinking reaction conditions.

Methods for crosslinking the structures will now be described with particular reference to FIGS. 13–16. In the reactions which are described in these figures, it will be understood that the polymer compounds shown are part of an ordered surface array of compounds in a vesicular or micellar structure, and that the compounds may be separated by one or more lipids which are part of these structures, but which themselves are not crosslinked in the crosslinking reaction.

Figure 13:
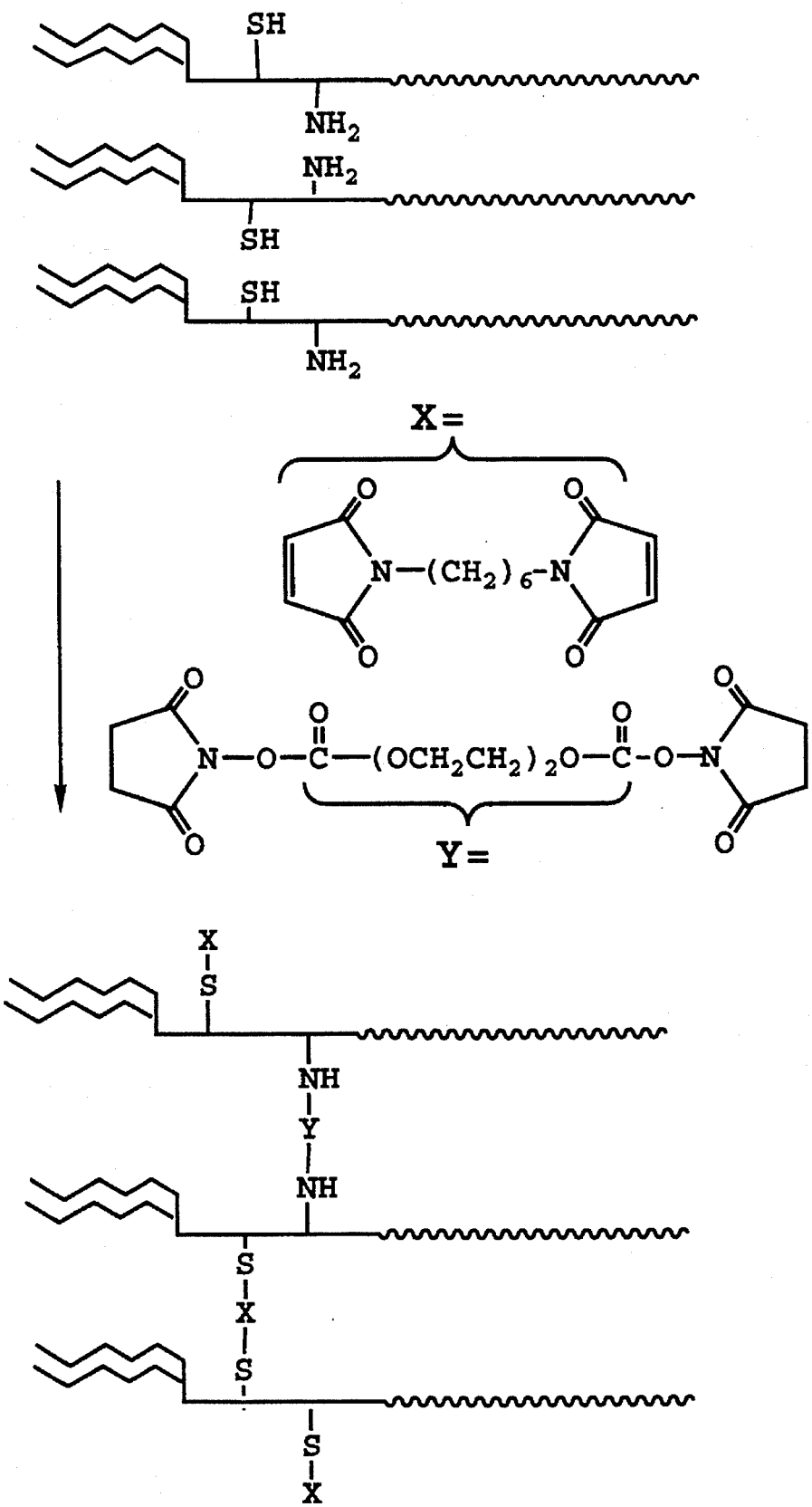
FIG. 13 illustrates a step in forming crosslinking structures between adjacent polymer compounds whose linking segments contain both amine and sulfhydryl groups.

FIG. 13 illustrates a crosslinking reaction for polymer compounds which include, in their linking segments, both amine and sulfhydryl chemical groups. In the figure, the region to the right is the hydrophilic exterior of a vesicular or core particle, and is thus the region exposed to the aqueous medium in which the particles are suspended, and in which the crosslinking reagents are in contact with the structures. In the crosslinking reactions illustrated in FIG. 13, the medium is first exposed to reducing conditions, to minimize disulfide linkage formation between adjacent sulfhydryl groups in the linking segments. The structures are then reacted with a bifunctional reagent, such as a bismaleimide, effective to crosslink sulfhydryl groups. Bifunctional agents suitable for crosslinking sulfhydryl groups are discussed generally in Wong, pp. 104–122, and suitable reaction conditions are provided by the reference.

After sulfhydryl group crosslinking, the crosslinking agent is preferably removed, and a second bifunctional reagent, such as a disuccinimidyl carbonate of diethylene glycol, capable of crosslinking amine groups is added. Reagents and reaction condition suitable for crosslinking amine are discussed generally in Wong, pp. 75–104. Example 5 gives reaction conditions for the two coupling reactions shown in FIG. 13.

FIG. 14 illustrates another crosslinking reaction for polymer compounds. As shown, the polymer compounds contain amine groups in their linking segments. Amine groups on adjacent polymer compounds can be crosslinked to form a crosslinked surface using a hydrophilic crosslinking reagent with bifunctional active esters or active carbonates, such as a disucinnimidyl carbonate of PEG (Zalipsky, 1992). Reaction conditions are provided in Example 6. Other N-hydroxydicarboximide derivatives, such as N-hydroxyphthalimide or disuccinimidyl suberate are also suitable.

In another embodiment, a linking segment with amine groups can react with dithiobis-(succinimidylpropionate), to incorporate a disulfide bridge into each crosslinking structure. The disulfide bridges in the crosslinking structure may be reduced in vivo to open the crosslinked surface and accelerate drug release from the particles.

Figure 15A:
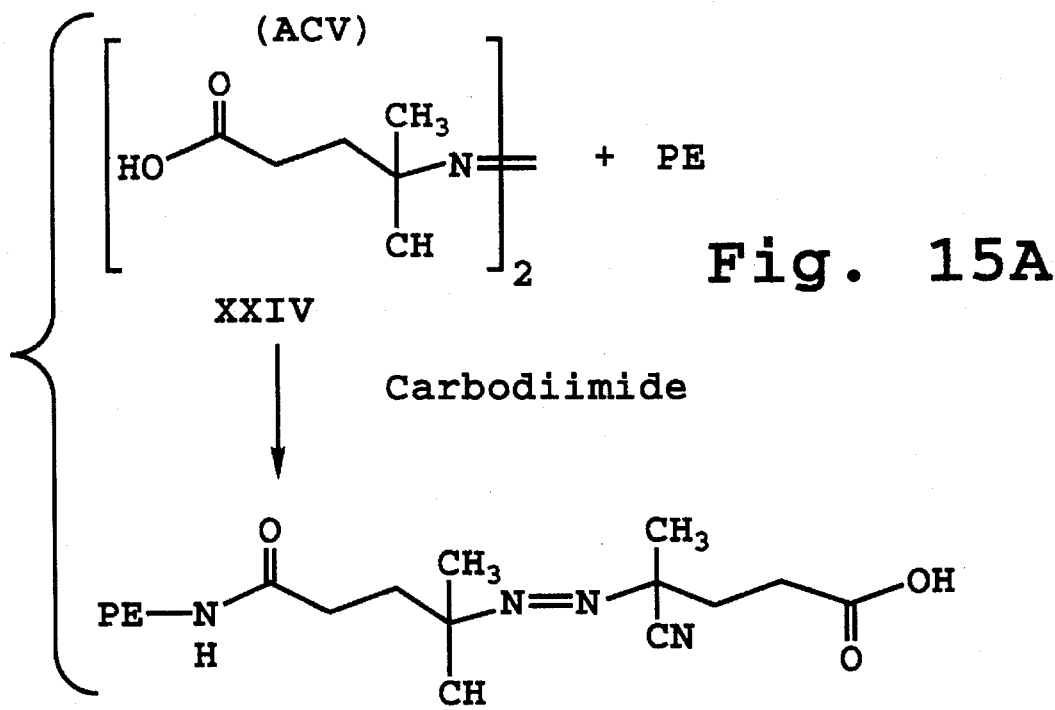
FIGS. 15A and 15B illustrate steps in forming crosslinking structures between adjacent polymer compound whose linking segments contain a vinyl group, where
Figure 15B:
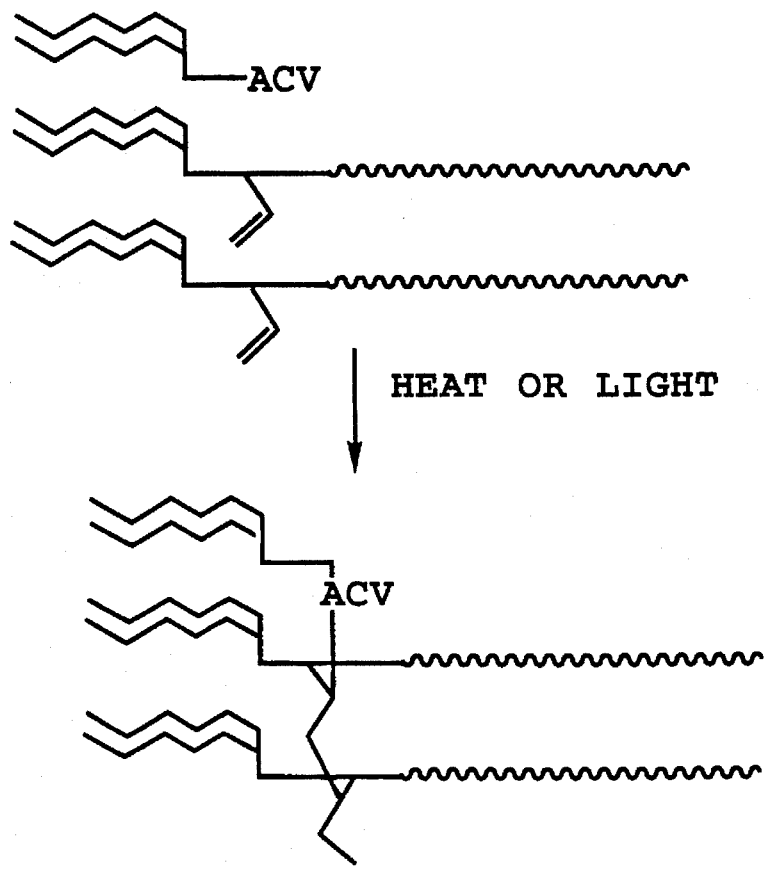

FIGS. 15A and 15B illustrate steps to crosslink polymer compounds whose linking segments contain vinyl groups. FIG. 15A shows the preparation of a radical initiator compound that can be included in a liposome composition for use in initiating a radical polymerization reaction at the structure surface. 4,4'-azobis-(4-cyanovaleric acid) (ACV) (compound XXIV) is conjugated to the amine group of a phospholipid, such as phosphatidylethanolamine (PE) to form compound XXV. Alternatively, a phospholipid derivative, such as a phosphatidylserine-PEG derivative may be conjugated to ACV.

FIG. 15B shows the crosslinking of the polymer compounds after initiation of a radical polymerization reaction by initiator compound included in a lipid structure at about 0.01–1 mole percent of the total lipid composition. The vinyl groups on adjacent polymer compounds are crosslinked to form a crosslinked surface by radical polymerization initiated by the radical initiator compounds using heat or light. Reaction conditions are described in Example 7.

FIG. 16 illustrates a crosslinking reaction for first and second polymer compounds which include linking segments with amine and sulfhydryl groups, respectively. These two polymer compounds can be crosslinked by use of a bifunctional crosslinking reagent, such as maleimidobenzoyl-N-hydroxysuccinimide ester (MBS), which contains at one end a group reactive with amine groups and at the other end a group reactive with sulfhydryl groups. Reaction conditions are given in Example 8. In other embodiments of the invention, the polymer compound has a linking segment and a hydrophobic moiety formed by a sphingolipid or phospholipid. Hydroxyl groups of either DSPI, $GM_1$ or $GM_3$ can be oxidized in the presence of periodate to aldehydes. Alternatively, hydroxyl groups of gangliosides can also be oxidized by galactose oxidase (Moss).

Aldehyde groups on adjacent polymer compounds are then crosslinked by a reductive amination reaction using an amine-containing compound, such as PEG200 bis amine. Bifunctional hydrazides, for example, adipic dihydrazides, can also serve as suitable reagents for crosslinking multiple aldehyde groups.

The crosslinking reactions described above, or other well-known coupling reactions may also be employed in linked target molecules and/or drug molecules to the outer surface of the particles, typically to the free (distal) ends of the hydrophilic polymers, which in this general embodiment, are provided with reactive free ends, such as OH or amine groups. Typically, targeting molecules, such as peptide or glycopeptide antigens, are typically attached to the hydrophilic polymers by non-labile covalent bonds. Drug compounds, by contrast, may be preferably attached to the polymers by labile bonds, e.g., disulfide or ester bonds, which allow drug release from the circulating particles, or at a target site.

After preparation of a crosslinked particle surface, vesicle-forming lipids may be removed from the crosslinked surface particles upon addition of a detergent, such as deoxycholate, or a water-miscible organic solvent, such as ethanol, to the aqueous medium forming a vesicular pharmaceutical composition in accordance with the invention. Where the particle is formed by polymer addition to a solid particle, the particle may be removed after crosslinking by exposure to a suitable solvent or enzyme capable of hydrolysing the particle.

From the foregoing, it will be appreciated how various objects and features of the invention are met. The particles of the invention are long-circulating, by virtue of their defined sizes and hydrophilic polymer coating, and thus are effective for targeting via the bloodstream, e.g., such as tumor targeting. The particles are readily formed with desired sizes, preferably between about 0.05 and 0.2 microns, which can be made quite homogeneous in size employing conventional lipid-vesicle extrusion methods. For tumor targeting, the particles preferably have selected sizes in the 0.07 to 0.12 size range, allowing particle extravasation into tumors, as described in co-owned U.S. Pat. No. 5,213,804.

The invention encompasses crosslinked particles which can be loaded with either hydrophilic or hydrophobic drugs, and in both cases, the degree of crosslinking on the particle surface can be selectively varied to vary the rate of release of encapsulated drug from the particles.

The following examples illustrate methods of preparing polymer compounds and pharmaceutical compositions. The examples are intended to illustrate specific polymer compounds and pharmaceutical compositions of the invention, but are in no way intended to limit the scope thereof.

EXAMPLE 1

Preparation of PEG-poly(D,L-lysine)-DSPE

A PEG polymer is reacted with N-carboxyanhydrides of lysine whose epsilon lysine group have been protected with a formyl group. The derivatized polymer is then linked to DSPE. The procedure is illustrated in FIG. 3.

First, lysine (Lys) is formylated at its epsilon-amine group at 5° C. by adding ethyl formate. Lys (5.2 g) is dissolved in ice-cold 1N sodium hydroxide (60 ml) and methanol (60 ml) is added. Ethyl formate (24 ml) is added and the mixture is stirred for 2 hours. The pH of the mixture is checked periodically and 5N NaOH is added periodically to maintain the pH between 8 and 9. The organic solvents are removed in vacuo. The product is then suspended in water, and ethanol is added to bring about precipitation.

The purified and thoroughly dried $N\epsilon$-formyl-Lys is then converted into its NCA derivative using the classical phosgenation reaction (Bodanszky).

mPEG2,000 monoamine (100 mmole) is dissolved in an aqueous solution at low temperature and pH 7. To this is added 400 mmole of $\epsilon$-formyl NCA-lys. The reaction is allowed to proceed 3 hours. Water is removed in vacuo. The product is recrystallized from ethanol.

DSPE (100 mmole) in chloroform is first treated with glutaric anhydride and the product is coupled with the PEG derivative (100 mmole) in the presence of dicyclohexylcarbodiimide (DCC) and hydroxybenzatriazole (HOBt). The mixture is maintained on an oil bath at about 37° C. overnight.

The formyl protecting groups on lysine are removed by reaction with 5% aqueous hydrazine acetate (Hofmann).

EXAMPLE 2

Preparation of Polymer Compound with Sulfhydryl Groups

A $PEG-NH_2$ is first reacted with N-carboxyanhydride of cysteine whose sulfhydryl group is protected by thiopyridine to form a PEG derivative containing multiple protected sulfhydryl groups. The PEG derivative is linked to DSPE. The procedure is illustrated in FIG. 4.

NCA derivative of thiopyridine-S-protected cysteine (NCA-cys) was prepared as described (Bodanszky).

mPEG2,000 monoamine (100 mmole) is dissolved in an aqueous solution at low temperature and pH 7. To this is added 400 mmole of S-thiopyridine NCA-cys derivative. The reaction is allowed to proceed 3 hours. Water is removed in vacuo. The product is recrystallized from ethanol.

DSPE (100 mmole) in a chloroform suspension is first treated with glutaric anhydride and the product is coupled with the PEG derivative (100 mmole) in the presence of dicyclohexylcarbodiimide (DCC) and hydroxybenzatriazole (HOBt). The mixture is maintained on an oil bath at about 37° C. overnight.

The thiopyridyl protecting groups on cysteine are removed by reduction with dithiothreithol (DTT).

EXAMPLE 3

Preparation of polymer Compound with a Sulfhydryl Group and an Amine Group in a Linking Segment N-formyl lysine methyl ester is prepared as described by Hofmann et al and reacted with monomethoxy PEG chloroformate prepared by reaction of monomethoxy PEG monoalcohol with phosgene (Zalipsky, 1992). The methyl ester of the product is saponified and the exposed carboxyl coupled with homocysteine thiolactone to form a polymer with a terminal thiolactone ring. DSPE can react at neutral pH in the presence of silver ion at the thiolactone ring to generate a free sulfhydryl group. The product's epsilonamino group is deprotected by standard methods. The procedure is illustrated in FIG. 6.

Monomethoxy PEG chloroformate is formed by reacting methoxypolyethylene glycol in toluene/dichloromethane and treated with a toluene solution of phosgene. The solution is evaporated overnight and the remainder phosgene evaporated under vacuum (Zalipsky, 1992). Homocysteine thiolactone reacts readily with the deprotected carboxyl group to form a polymer with a terminal thiolactone ring. DSPE can react at neutral pH in the presence of silver ion at the thiolactone ring to generate a free sulfhydryl group. The formyl protecting groups on lysine are removed by reaction with 5% aqueous hydrazine acetate (Hofmann).

EXAMPLE 4

Preparation of Polymer Compound with a Vinyl Group in its Linking Segment 10 mmol monomethoxy PEG is dissolved in 40 ml anhydrous benzene and cooled in a bath of crushed ice. 1.53 ml (11 mmol) triethylamine and 1.85 ml (11 mmol) of trifluoroethane sulfonyl chloride are added and the mixture is stirred overnight under an inert atmosphere.

The solvent is then evaporated under reduced pressure and the residual syrupy paste is diluted to 100.0 ml with methylene chloride.

To 0.5 mmole product is added 3.72 ml of a chloroform solution containing 372 mg (0.5 mmoles) egg PE. To the resulting solution, 139 microliters (1.0 mmole) of triethylamine is added and the solvent is evaporated under vacuum. To the obtained residue, 5 ml dry dimethyl formamide and 70 microliters (0.50 mmoles) triethylamine is added. Air from the reaction vessel is displaced with nitrogen. The vessel was closed and heated in a sand bath a 110° C. for 22 hours. The solvent was evaporated under vacuum to obtain desired product.

PE-PEG compound (1 mmole) is dissolved in 2 ml of chloroform and triethylamine. To this, 1 mmole acryloyl chloride is added. The resulting solution is let to stand for 3 days at 23° C. The solvent from the reaction mixture is evaporated under vacuum and dried to constant weight.

EXAMPLE 5

Crosslinking Amine and Sulfhydryl Group Containing Linking Segments by Thioether and Amide Linkages Two adjacent polymer compounds are initially crosslinked by addition of a bifunctional reagent, such as bismaleimidohexane, which reacts with the free sulfhydryl groups. The amine groups are crosslinked with a bifunctionalized reagent, such as disuccinimydyl carbonate of diethylene glycol. Liposomes in an aqueous buffered solution under nitrogen are incubated with bismaleimidohexane for several hours to crosslink sulfhydryl groups. Unreacted reagent is removed from the liposomes by gel filtration. Amino groups are crosslinked with disuccinimidyl suberate or disuccinimidyl carbonate of diethylene glycol.

EXAMPLE 6

Crosslinking Amine Group Containing Linking Segments by Amide Linkages

Liposomes in an aqueous buffer pH 8 are incubated with an equivalent amount of disucinnimidyl carbonate of diethylene glycol (Zalipsky, 1992) for direct crosslinking of adjacent polymer compounds. The reaction is allowed to proceed at room temperature for 2 hours while the pH 8 is maintained by titration with 0.5N sodium hydroxide.

EXAMPLE 7

Crosslinking Vinyl Group Containing Linking Segments by Radical Polymerization

For crosslinking of vinyl-group containing linking segments of adjacent polymer compounds in a liposome the following procedure is employed and illustrated in FIGS. 15A and 15B (Otsu, Ito).

A radical polymerization initiator which can be incorporated into liposomes is synthesized by reacting ACV with PE in the presence of carbodiimide.

Liposomes containing 0.01 mole percent of the initiator-derivatized lipid and the vinyl group-containing polymer compound in an aqueous buffer pH 6 are incubated at 37° C. for 3 hours.

EXAMPLE 8

Crosslinking Amine Group Containing Linking Segments with Sulfhydryl Group Containing Linking Segments by a Heterobifunctional Reagent Particle compositions in this example include two polymer compounds. One contains multiple sulfhydryl groups, generated, for example, from a polycysteine linking segment. Another polymer compound contains multiple amine groups generated from a polylysine linking segment as described above. These two types of polymer compounds can be crosslinked to each other by use of a heterobifunctional crosslinking reagent, such as m-maleimidobenzoyl-N-hydroxysuccinimide ester (MBS) as illustrated in FIG. 16.

Liposomes in an aqueous buffer pH 8 under nitrogen are incubated MBS for crosslinking of amine groups and sulfhydryl groups on adjacent polymer compounds. The reaction is allowed to proceed at room temperature for 2 hours while pH 8 is maintained by titration with 0.5N sodium hydroxide.

Although the invention has been described and illustrated with respect to particular polymer compounds and polymer particles, it will be apparent that a variety of modifications and changes may be made without departing from the invention.

It is claimed:

1. A pharmaceutical composition for use in the parenteral delivery of a pharmaceutical compound, said composition comprising particles having a selected uniform size in a size range between 0.03–1.0 microns, each particle including (a) a single layer of linked polymer compounds composed of an outer hydrophilic polymer, an inner hydrophobic moiety, and a linking segment linking the polymer to the hydrophobic moiety and containing at least two chemical groups by which the compound can be crosslinked to at least two other compounds, (b) a crosslinked particle surface coated by said hydrophilic polymers, said crosslinked surface formed by a crosslinking structure created by crosslinks between said chemical groups, and (c) said pharmaceutical compound entrapped in said particle.

2. The composition of claim 1, wherein said hydrophobic moiety is a vesicle-forming lipid moiety.

3. The composition of claim 2, wherein said vesicle-forming lipid moiety is a phospholipid whose polar head group is covalently attached to said linking segment.

4. The composition of claim 1, wherein said hydrophilic polymer is polyethylene glycol.

5. The composition of claim 1, wherein the chemical groups in each linking segment include, in non-crosslinked form, sulfhydryl groups, and said crosslinking structure includes disulfide or thioether linkages with the chemical groups.

6. The composition of claim 1, wherein the chemical groups in each linking segment include, in non-crosslinked form, amine groups, and said crosslinking structure includes amide linkages with the chemical groups.

7. The composition of claim 1, wherein said linked polymers include first and second linked polymers having first and second different chemical groups, respectively, in non-crosslinked form, and the crosslinking structure crosslinks the different chemical groups on adjacent first and second linked polymers.

8. The composition of claim 7, wherein said first and second linked polymers have, as their chemical groups in non-crosslinked form, sulfhydryl and amine groups, respectively, and said crosslinking structure includes bridges linking the sulfhydryl groups, through disulfide or thioether linkages, to the amine groups, through amide linkages.

9. The composition of claim 1, wherein the particle further includes a radical initiator compound attached to the particle surface, and the chemical groups in each linking segment include, in non-crosslinked form, vinyl groups, and said crosslinking structure includes carbon-carbon bonds derived from vinyl group polymerization initiated from the initiator compound.

10. The composition of claim 1, wherein the chemical groups include first and second different chemical groups, in non-crosslinked form, and the crosslinking structure crosslinks similar chemical groups on adjacent linked polymers.

11. The composition of claim 10, wherein the chemical groups include, in non-crosslinked form, sulfhydryl and amine groups, and said crosslinking structure includes bridges linking the sulfhydryl groups, through disulfide or thioether linkages, to other sulfhydryl groups and linking the amine groups, through amide linkages, to other amine groups.

12. The composition of claim 1, wherein said particles are vesicular particles having an aqueous interior, and said pharmaceutical compound is a water-soluble compound entrapped in said interior volume.

13. The composition of claim 1, wherein the pharmaceutical compound is a polypeptide.

14. The composition of claim 1, wherein the particles are lipophilic-core particles having a lipophilic interior core, and said pharmaceutical compound is a lipophilic compound entrapped in said interior volume.

15. A method for preparing a pharmaceutical composition composed of particles having a selected uniform size between about 0.03–1.0 microns, for use in parentoral administration of a particle-entrapped pharmaceutical compound, said method comprising (a) preparing, in an aqueous medium, lipid structures composed of a polymer compound having an outer hydrophilic polymer, an inner hydrophobic moiety, and a linking segment linking the polymer to the hydrophobic moiety and containing at least two chemical groups by which the compound can be crosslinked to at least two other compounds, and (b) crosslinking the chemical groups in the linking segments of the polymer compounds.

16. The method of claim 15, wherein the structures are vesicular lipid structures formed by suspending in an aqueous medium, a mixture of 1–30 mole percent of the polymer compound and between 70–99 mole percent vesicle-forming lipids, and said forming further includes sizing the lipid structures to the selected particle size, and which further includes, after said crosslinking, removing said vesicle-forming lipids from the particles.

17. The method of claim 16, wherein said forming includes encapsulating such a pharmaceutical compound in the vesicular lipid structures.

18. The method of claim 15, wherein said structures are core lipid structures formed by suspending the polymer compound in an aqueous medium at a concentration above the critical micelle concentration of the compound.

19. The method of claim 15, wherein the chemical groups in the linking segment of each polymer compound are amine and sulfhydryl groups, and said crosslinking includes linking said sulfhydryl groups to one another through disulfide or thioether linkages, and linking the amine groups through amide linkages.

20. The method of claim 15, wherein the chemical groups in each linking segment include, in non-crosslinked form, amine groups, and said crosslinking includes reacting said groups with a bridging reagent having two or more activated carboxylic acid groups.

21. The method of claim 15, wherein the lipid structures are formed to include first and second polymer compounds having first and second different chemical groups, respectively, and said crosslinking includes reacting the vesicular structures with a bridging reagent having at least one reactive group which is reactive with said first chemical group, and at least one other reactive group which is reactive with said second chemical group.

* * * * *